US006821692B1

(12) United States Patent
Ermantraut et al.

(10) Patent No.: US 6,821,692 B1
(45) Date of Patent: Nov. 23, 2004

(54) KIND OF THIN FILMS FOR MICROSYSTEM TECHNOLOGY AND MICROSTRUCTURING AND THEIR USE

(75) Inventors: Eugen Ermantraut, Jena (DE); Johann Michael Köhler, Golmsdorf (DE); Torsten Schulz, Jena (DE); Klaus Wohlfart, Laasan (DE); Stefan Wölfl, Jena (DE)

(73) Assignee: Clondiag Chip Technologies GmbH, Jena (DE)

( * ) Notice: Subject to any disclaimer, the term of this patent is extended or adjusted under 35 U.S.C. 154(b) by 0 days.

(21) Appl. No.: 09/230,975

(22) PCT Filed: Aug. 22, 1997

(86) PCT No.: PCT/EP97/04582

§ 371 (c)(1),
(2), (4) Date: Feb. 4, 1999

(87) PCT Pub. No.: WO98/08086

PCT Pub. Date: Feb. 26, 1998

(30) Foreign Application Priority Data

Aug. 23, 1996 (DE) .......................................... 196 34 120
Feb. 15, 1997 (DE) .......................................... 197 05 909

(51) Int. Cl.$^7$ ............................ G03F 7/023; G03F 7/30
(52) U.S. Cl. ........................... 430/17; 430/18; 430/165; 430/167; 430/191; 430/195; 430/196; 430/197
(58) Field of Search ..................... 430/17, 18, 165, 430/167, 191, 192, 196, 197

(56) References Cited

U.S. PATENT DOCUMENTS

| | | | | | |
|---|---|---|---|---|---|
| 3,884,703 A | * | 5/1975 | Oba et al. | .................... | 430/196 |
| 4,106,938 A | * | 8/1978 | Fletcher et al. | ............. | 430/152 |
| 4,251,620 A | * | 2/1981 | Oda et al. | .................. | 430/300 |
| 4,288,526 A | * | 9/1981 | Oda et al. | ................ | 430/272.1 |
| 4,451,568 A | * | 5/1984 | Schneider et al. | .......... | 435/181 |
| 4,472,494 A | * | 9/1984 | Hallman et al. | ............ | 430/160 |
| 4,923,948 A | * | 5/1990 | Matsuki et al. | ............... | 528/26 |
| 4,943,512 A | * | 7/1990 | Kawabata et al. | .......... | 430/197 |
| 4,960,722 A | * | 10/1990 | Ogawa | .......................... | 438/1 |
| 5,041,570 A | * | 8/1991 | Tochizawa et al. | ......... | 430/167 |
| 5,053,225 A | * | 10/1991 | Miyasaka et al. | .......... | 424/85.5 |
| 5,154,808 A | * | 10/1992 | Miyasaka et al. | ...... | 204/157.15 |
| 5,157,018 A | * | 10/1992 | Muller | ....................... | 528/493 |
| 5,202,227 A | * | 4/1993 | Matsuda et al. | ............ | 430/167 |
| 5,411,836 A | * | 5/1995 | Yoda et al. | .................. | 430/190 |
| 5,593,814 A | * | 1/1997 | Matsuda et al. | .............. | 430/14 |
| 5,725,978 A | * | 3/1998 | Miyazawa | .................... | 430/25 |
| 5,846,814 A | | 12/1998 | Galla et al. | ............. | 435/287.2 |
| 6,020,093 A | * | 2/2000 | Shibuya et al. | ............. | 430/167 |

FOREIGN PATENT DOCUMENTS

| | | | | |
|---|---|---|---|---|
| DE | 36 02 486 | | 7/1987 | |
| DE | 275 538 | | 1/1990 | |
| DE | 2 98268 | | 2/1992 | |
| EP | 01 16361 A2 | | 8/1984 | |
| EP | 02 46602 A2 | | 11/1987 | |
| EP | 02 46602 A3 | | 11/1987 | |
| EP | 0 286 118 | | 10/1988 | |
| EP | 1 104 883 | | 6/2001 | |
| FR | 73 33863 | | 9/1973 | |
| JP | 01241541 A | * | 9/1989 | ............ G03C/1/71 |
| WO | 94/28414 | | 12/1994 | |

OTHER PUBLICATIONS

Kosar, Jaromir, Light–sensitive Systems: Chemistry and Application of Nonsilver Halide Photographic Processes, 1965, pp 276,324, 331,336.*
Jan. 1, 1986 Supported planar membranes in studies of cell–cell recognition in the immune system H.M. McConnell et al. Biochimica et Biophysica Acta 864 pp. 95–106.
Feb. 1, 1994 Die Mikrosystemtechnik und ihre Anwendugsgebiete Von Wolfgang Menz Spektrum der Wissenschaft pp. 92–99.
Chemical Abstracts 125:45144.
Chemical Abstracts 107:106351.
Chemical Abstracts 84:82561.

* cited by examiner

*Primary Examiner*—John S. Chu
(74) *Attorney, Agent, or Firm*—Jordan and Hamburg LLP

(57) ABSTRACT

The present invention relates to novel thin layers for microsystem techniques and microstructuring. It is an object of the invention to provide thin layers which can be manufactured under less problems and more economically than the previous conventional layers, and which permit the use of existing technologies for microstructuring. The object is realized in that the thin layer is formed of an enzymatically degradable biopolymer in a range of layer thicknesses of from 30 nm to 3 μm. Biopolymeric thin layers manufactured according to the invention permit their application, after a respective structurizing, as test assays or in setting up substance libraries.

27 Claims, No Drawings

KIND OF THIN FILMS FOR MICROSYSTEM TECHNOLOGY AND MICROSTRUCTURING AND THEIR USE

BACKGROUND OF THE INVENTION

The present invention relates to novel thin layers for microsystem techniques and microstructuring which may be employed within the range of such technologies in various manners.

The thin layers heretofore employed according to the state of art in the microsystem technique and in microstructuring, as for example for manufacturing membranes, sandwiched system contacts and circuits are based on the use of inorganic layers, such as layers of $SiO_2$, $Si_3N_4$, and $Al_2O_3$ frequently employed, and metal layers and metal layer systems, respectively. Poisonous chemicals and such being harmful to health, as for example strong acids, alkalies, and oxidants, are employed to produce the desired structures, or extremely expensive processes, such as reactive ion etching and plasma etching, respectively, are required therefor (refer to S. Büittgenbach, Mikromechanik, B. G. Teubner, Stuttgart, 1994). The only organic layers which are to be used in structuring processes are photoresists which after the desired structure being imparted to the layer to be structurized are removed, as a rule.

SUMMARY OF THE INVENTION

It is an object of the present invention to provide thin layers which can be manufactured less critically and more economically than previous conventional thin layers under use of existing technologies in microstructuring and which are suited in a particularly advantageous manner for setting-up substance libraries.

SUMMARY OF THE INVENTION

The object is realized by the characteristic features of the first claim.

Advantageous embodiments are covered by the succeeding claims. It was found that in the field of microstructuring the masking layers capable of structurizing and employed previously to this end, such as photoresist layers, may locally affect the properties of biopolymer films, for example gelatin, agarose, dextrose, and lipid.

Furthermore, it was surprisingly found that it is feasible to produce such biopolymer films also within the range of thickness relevant for the thin layer techniques of from 30 nm to 3 µm to satisfy very high quality standards. Moreover, it was found that certain dyestuffs or photoactivatable groups effect a cross-linking of the biopolymer layer subsequent to a photochemical activation so that their enzymatic decomposition rate considerably slows down compared to unexposed layer ranges.

The layer thicknesses are reproducible within a range of a few 10 nm from solutions with a solids content from 1 to 30% by spin coating which itself is known. Layers applied in such a manner are even in such an extremely thin layer range unexpectedly homogeneous and free of defects. They also resist tempering steps of up to 250° C. without any problems and without any signs of degradation during the further process of microstructuring.

The main advantage of such layers from biopolymers, however, consists in their enzymatic degradability which results in a high specificity of degradation which generally takes place under moderate conditions, at ambience, and in solutions exhibiting a pH number preferably from 4 to 9. Basically biopolymers offer the advantage that they provide definite functions for coupling covalently, but also non-covalently further molecules and layers.

Thus, for example, it is feasible to couple to a gelatin layer by way of carboxy-, amino-, and thio-functions but also by way of hydrogen bridge linkages. Furthermore it is feasible without any problems to cross-link biopolymers (for example, by means of glutaric dialdehyde in the presence of a free keto-, amino-, or hydroxyl group), and, hence, to respectively vary the properties of the produced layer.

Thus, for example, a hydrosoluble gelatin changes to a water-insoluble material after a cross-linkage in that molecules are enclosed therein or, alternatively, are bound thereto covalently or non-covalently. Depending on their formation, the proposed thin layers, in the field of application concerned, can be used to various ends.

The following embodiments illustrate feasible applications in more detail.

DETAILED DESCRIPTION OF THE INVENTION

In a first embodiment the properties of enzymes as highly specified catalysts are utilized to generate a self-supporting novolac structure under use of a biopolymeric thin layer consisting of gelatin. To this end a gelatin layer of about 200 nm thickness is applied to a cleaned silicon wafer by spin-coating. In the present example, said layer is formed by gelatin (10% v/v) dissolved in water to which 5% glutaric dialdehyde is added. Said layer is not water-soluble and is resistant to conventional photoresist coating developers. A photo reversal resist as commonly on sale is applied to said layer also by means of spin-coating. Said photoresist layer is treated according to the instructions, masked according to a desired subsequent structure, exposed, and structurized. The entire sandwich assembly is inserted into a receptacle containing an enzymic bath. Provided that gelatin is utilized for the biopolymer layer the enzymic bath preferably consists of a protease K-buffer substantially constituted of 10% SDS, 10 mM NaCl, 10 mM EDTA and Tris-HCl, and to which 10 mg/ml protease K is added. The pH-value of said bath is set to 8.5. When such an enzymic bath is employed a gelatin layer of about 200 nm thickness is entirely degraded at ambient temperature within about 8 h. In the present example, the biopolymer layer was used as a sacrificial layer for generating a self-supporting novolac structure.

In a second embodiment which again, as the foregoing first example, is based on a sandwich assembly constituted of gelatin and a photoresist, the property of enzymes as being highly specific catalysts is utilized, the functions of which are inhibited by suitable inhibitors and competitors, respectively. Accordingly, diazo-naphthoquinone, which is in AZ-photoresists a usual photosensitive component, binds to OH-groups of the gelatin and, hence, inhibits a protease applied in a buffer solution of being degraded. When exposed diazo-naphthoquinone is converted into a carboxyl acid which is salified and separated from the gelatin. At such locations the degradation can take place uninhibited. Hence, the degradation is achieved "anisotropically" in analogy to the previous selective etching techniques. At places where the inhibitor is still present the degradation speed is considerably reduced. Thus it is feasible to use biopolymers and the suitable degradation enzymes and modification enzymes, respectively, as a component of microsystem techniques as well as a mask material.

A third embodiment provides the potentiality to add a light sensitive conditioner (for example, diazonaphthoquinone) to the biopolymeric thin layers to generate a layer which is applicable itself as a photoresist. This involves the condition that the light sensitive additive either acts as an inhibitor itself to the enzyme to be degraded or is coupled to such an inhibitor. Due to this embodiment being at one's disposal it is feasible to produce photoresists which can be developed enzymatically.

A fourth embodiment will describe the manufacturing of a lipid layer of about 100 nm thickness. To this end a solution consisting of phosphatidyl-ethanolamine in cloroform (0.1 g/ml) is spun onto a suitable substrate at 5000 revolutions per minute for 30 s.

According to a fifth embodiment it is feasible to coat a thin layer of gelatin to which is added a biogenic inhibitor of protease function, such as TFPI (tissue factor pathway inhibitor) mixed 1:1000 parts by weight, with pure gelatin. This provides for an etching stop in the case of a subsequent enzymatic treatment. In analogy thereto, a degradation stop can be incorporated in layers consisting of agarose, dextroses, and lipids by selecting a substance which exhibits an inhibiting effect to a later added enzyme.

While the foregoing embodiments are in concern of the formation of thin layers, the application of which is comparable to a known positive photoresist according to the state of art, a sixth embodiment of a thin layer according to the present invention will be described hereinafter, which compares to a negative resist.

For example, di-acidostilbene, being dissolved in water and having its maximum sensitivity at about 345 nm, is employed as a photoactive component with a spectral sensitivity in the visible or in the ultraviolet spectral range, wherein a sodium salt of 4,4-di-acidostilbene-2,2-sulpho acid which has been dissolved in water at a mixing ratio of from 1:50 to 1:100 has proven as particularly advantageous. A solid gelatin, for example Quality Bloom 60 made of pigskin is added to the aqueous di-acidostilbene solution at a quantity ratio of from 10:1 to 100:1, depending on the desired degree of cross-linking in the biopolymeric layer to be produced. In the present example, about 40 mg gelatin per ml. di-acidostilbene solution are added. After the gelatin has dissolved the solution is filtered through a microfilter to 200 nm. The solution obtained in this way is spun onto a substrate, for example, consisting of a metal, a polymer, silicon, coated silicon or glass, as common use in microlithography. In this manner according to the present example a plane homogeneous gelatin layer having a thickness of about 100 nm is formed on a silicon substrate. The thin layer is provided with a mask adapted to a subsequent and desired structure and is subjected to an UV-exposure at a wavelength of 360 nm for about 400 s. This results in the acido-groups of the diacidostilbene being photochemically split up to a bisnitrene-radical under splitting-off of nitrogen leading to a linkage of the amino-acid chains of the gelatin in the exposed ranges. The development of the exposed gelatin layer is carried out under water which results in a coarse frilling of the unexposed ranges of the gelatin layer already after 1 to 2 min. This is followed by a redevelopment in a protease buffer solution having a concentration of 0.1 mg/ml buffer-solution which, in the present example, consists of 10% sodium lauryl sulphate, 10 mM NaCl, 10 mM EDTA, Tris-HCl at an alkalescent pH-value of about 8.5.

The degradation rates obtainable in the present example lie at about 20–30 nm/min. According to the manner described hereinabove, it is feasible to produce sizes of structures down to 1 $\mu$m.

The manner of producing the cross-linking of exposed ranges according to the present invention permits the generation of even more stable structures than the respective positive structures produced by the embodiments one to five.

The advantage of biopolymers to provide defined functions for covalent but also non-covalent coupling to further molecules (so, for example, it is feasible to couple to a gelatin layer by way of amino-, carboxy-, hydroxy-and thio-functions but also by way of hydrogen bridge linkage), can be particularly advantageously exploited in thin layer structures suitably structurized and generated according to the above specifications for a special application, as will be described in the following.

It is feasible to generate regular arrays of squares on a supporting substrate in starting from a gelatin layer produced according to the foregoing specifications, imposing a mask, for example, of chessboard pattern thereupon and carrying out the exposure and development in analogy to the above described. Assuming an edge length of, for example, 16 $\mu$m for the squares then the latter have a depth of structure of 18 nm after completion of the foregoing developing process. Microstructures (pads) produced in this manner and having predetermined positions of linkage made of gelatin and allied collagens, respectively, are particularly suited for setting up screening tests and substance libraries in the field of biotechnology, molecular biology, pharmacy, and medicine. Such libraries are for finding and quickly locating interacting participants in the molecular field. It is very easy to couple proteins (for example, antibodies) or respectively modified oligonucleotides to the microstructurized gelatin pads via a peptide linkage, which enables to build up, for example, test assays.

Local reaction spaces are defined by way of structurized gelatin pads. Due to the chemical diversity of the functional groups of the collagen polymer it is feasible to bind diverse molecules after a specific activation. In other words, the same matrix can be utilized for coupling molecules having a diversity of functional groups, the expensive modification of the molecules for immobilization is omitted.

What is claimed is:

1. A microstructurable thin layer consisting essentially of an enzymatically degradable biopolymer having an inhibitor or a competitor of the enzymatic degradability of said biopolymer on at least part of its surface, the thin layer having a thickness of 30 nm to 3 $\mu$m, said layer being enzymatically degradable by a suitable individual enzyme.

2. A microstructurable thin layer consisting essentially of an enzymatically degradable biopolymer intermingled with an inhibitor or a competitor of the enzymatic degradability of said biopolymer, the thin layer having a thickness of 30 nm to 3 $\mu$m, said layer being enzymatically degradable by a suitable individual enzyme.

3. A microstructurable thin layer according to claim 1 or 2, wherein the biopolymer consists of gelatin.

4. A microstructurable thin layer consisting essentially of an enzymatically degradable biopolymer consisting of agarose and having an inhibitor or a competitor on at least part of its surface, or said biopolymer intermingled with an inhibitor or a competitor, the thin layer having a thickness of 30 nm to 3 $\mu$m, said layer being enzymatically degradable by a suitable individual enzyme.

5. A microstructurable thin layer consisting essentially of an enzymatically degradable biopolymer consisting of dextrose and having an inhibitor or a competitor on at least part of its surface, or said biopolymer intermingled with an inhibitor or a competitor, the thin layer having a thickness of 30 nm to 3 $\mu$m, said layer being enzymatically degradable by a suitable individual enzyme.

6. A microstructurable thin layer consisting essentially of an enzymatically degradable biopolymer consisting of a lipid and having an inhibitor or a competitor on at least part of its surface, or said biopolymer intermingled with an inhibitor or a competitor, the thin layer having a thickness of 30 nm to 3 μm, said layer being enzymatically degradable by a suitable individual enzyme.

7. A microstructurable thin layer for microsystem technology and microstructuring consisting essentially of one degradable biopolymer enzymatically degradable by a suitable individual enzyme, the one degradable biopolymer being selected from the group consisting of gelatin, agarose, dextrose and a lipid, the biopolymer being cross-linked and combined with an inhibitor or a competitor affecting a degradation function of said individual enzyme.

8. A method for producing a structured thin layer from an enzymatically degradable biopolymeric thin layer comprising
 (a) forming a biopolymeric layer comprising a biopolymer solution and a light sensitive conditioner on a substrate, said conditioner being an inhibitor of enzymatic action,
 (b) exposing the biopolymeric layer to ultraviolet radiation, which causes said conditioner to be more soluble in water,
 (c) separating said more soluble conditioner from the exposed biopolymeric layer, and
 (d) removing the exposed biopolymeric layer by washing with an aqueous solution and an enzymatic buffer solution.

9. A method according to claim 8, in which the biopolymer consists of one selected from the group consisting of gelatin, agarose, dextrose and a lipid.

10. A method according to claim 8, in which the biopolymeric layer is applied onto the substrate by spin casting.

11. A method according to claim 10, in which the spin casting is from a solution of the biopolymer of a solids content of 1 to 30%.

12. A method according to claim 11, in which the cross-linking agent is at least one of glutaric dialdehyde and formaldehyde.

13. A method according to claim 12, in which the cross-linking agent is added to the spin casting solution in a percentage of 1 to 5%.

14. A method according to claim 9, in which the conditioner is a diazo-naphthoquinone dye, the biopolymer consists of gelatin and the enzyme in the enzymatic buffer solution is a protease.

15. A structured enzymatically degradable biopolymer thin layer produced by the method of any one of claim 8, 9, or 14.

16. A method for producing a structured thin layer from an enzymatically degradable biopolymeric thin layer comprising:
 (a) forming a layer comprising a biopolymer solution, a thermally activatable cross-linking agent, and a photo-activatable radical agent for chain prolonging or linking, on a substrate thereby to form a cross-linked biopolymeric layer on the substrate,
 (b) exposing the biopolymeric layer to ultraviolet radiation, and then
 (c) removing unexposed biopolymeric layer by washing with an aqueous solution and an enzymatic buffer solution.

17. A method according to claim 16 in which the biopolymer consists of one selected from the group consisting of gelatin, agarose, dextrose and a lipid.

18. A method according to claim 16 or 17, in which the layer is applied onto the substrate by spin casting.

19. A method according to claim 18, in which the spin casting is from a solution of the biopolymer of a solids content of 1 to 30%.

20. A method according to claim 16, in which the cross-linking agent is at least one of glutaric dialdehyde and formaldehyde.

21. A method according to claim 19, in which the cross-linking agent is added to the spin casting solution in a percentage of 1 to 5%.

22. A method according to claim 19, in which the biopolymer consists of gelatin and the radical agent is added to the gelatin layer in such quantity that a ratio of gelatin to radical agent is 10:1 to 100:1.

23. A structured enzymatically degradable biopolymer thin layer produced by the method of claim 16.

24. A method according to claim 8, in which in (a), the biopolymer solution is applied onto the substrate and then the dye is added thereto.

25. A method according to claim 8, in which in (a), the dye is added to the biopolymer solution and then the biopolymer solution containing the dye is applied onto the substrate.

26. The method of claim 8, wherein said biopolymer is gelatin, said conditioner is a diazo-naphthoquinone dye which binds to the OH groups of the gelatin and inhibits the degradation function of a protease enzyme in a later applied buffer solution, the exposure of the biopolymer layer to ultraviolet radiation converts the diazo-naphthoquinone dye in the exposed portion of the layer to a carboxylic acid which is salified and removed from the biopolymeric layer, and the exposed portion of said layer, now free of the azo-naphthoquinone dye inhibitor, is degraded and removed by treatment with said protease enzyme buffer solution.

27. The method of claim 17 wherein said biopolymer is gelatin and the enzyme in said enzymatic buffer solution is a protease.

* * * * *